United States Patent [19]

Freiberg

[11] 3,970,642
[45] July 20, 1976

[54] PROCESS FOR THE CONVERSION OF NIDDAMYCIN TO LEUCOMYCIN A₁, LEUCOMYCIN A₃, CARBOMYCIN B AND OTHER ANTIBIOTICS AND RELATED 3-O-ESTERS

[75] Inventor: Leslie Alan Freiberg, Waukegan, Ill.

[73] Assignee: Abbott Laboratories, North Chicago, Ill.

[22] Filed: June 3, 1974

[21] Appl. No.: 476,016

[52] U.S. Cl.................................. 536/17; 424/180
[51] Int. Cl.²........................................ C07H 15/04
[58] Field of Search....... 260/210 AB, 210 K, 210 R

[56]  References Cited
UNITED STATES PATENTS

| | | | |
|---|---|---|---|
| 3,784,447 | 1/1974 | Therlault..................... | 260/210 AB |
| 3,792,035 | 2/1974 | Fukatsu et al................ | 260/210 AB |

OTHER PUBLICATIONS

Gaylord, "Reduction w/Complex Metal Hydrides," Interchemical Corp., N.Y., N.Y., 1956, p. 1.
Wagner and Zook, *Syn. Org. Chemistry*, pp. 261, 262 and 293, Wiley and Sons Inc., New York, 1953.
Gaylord, *Reduction with Complex Metal Hydrides*, pp. 308, 289 and 290, Interscience Publisher's Ltd., N.Y., N.Y., 1956.

*Primary Examiner*—Johnnie R. Brown
*Assistant Examiner*—Cary Owens
*Attorney, Agent, or Firm*—Vincent A. Mallare; Robert L. Niblack

[57]  ABSTRACT

Covers the process for the conversion of niddamycin to known compounds such as carbomycin B, leucomycin $A_1$ and $A_3$, and other antibiotic compounds as well as novel 3-(O)-esters and dimethyl acetal derivatives not obtained from natural sources. These compounds are represented by the general formula:

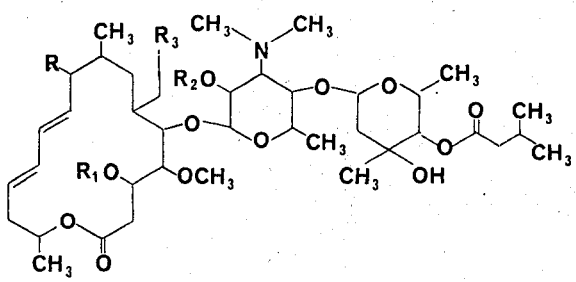

wherein R is hydroxy or oxygen, $R_1$ is hydrogen, HCO (formyl), $CH_3CO$ (acetyl), $CH_3CH_2CO$ (propionyl) or $CH_3CH_2CH_2CO$ (butyryl); wherein $R_2$ is hydrogen or equivalent to $R_1$ and $R_3$ is CHO or $CH(OCH_3)_2$.

These compounds are useful antimicrobial agents.

25 Claims, No Drawings

PROCESS FOR THE CONVERSION OF NIDDAMYCIN TO LEUCOMYCIN $A_1$, LEUCOMYCIN $A_3$, CARBOMYCIN B AND OTHER ANTIBIOTICS AND RELATED 3-O-ESTERS

This invention relates to a process for the synthesis of 16-membered macrolide antibiotic compounds. More particularly, it relates to the synthesis of leucomycin $A_1$ and related known and novel 3-(O)-esters and dimethyl acetal derivatives thereof and related known and novel 3-(O)-esters of niddamycin including carbomycin B and dimethyl acetal derivatives thereof that are active in inhibiting microorganism growth such as *Staphylococcus aureus* Wise 155, *Mycoplasma gallispeticum* S6, and *Haemophilus influenza*. The compounds of the present invention are derived from a series of conversions of niddamycin. The compounds obtained from this process have the structural formula:

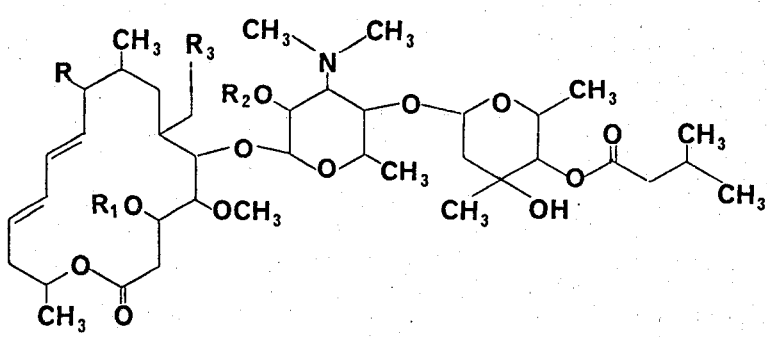

wherein R is hydroxy or oxygen; $R_1$ is hydrogen, formyl, acetyl, propionyl or butyryl; $R_2$ is hydrogen or equivalent to $R_1$ and $R_3$ is CHO or $CH(OCH_3)_2$. In the carbomycin B compound, R is oxygen, $R_1$ is acetyl, $R_2$ is hydrogen and $R_3$ is CHO. In the compound leucomycin $A_1$, R is hydroxy, $R_1$ and $R_2$ are hydrogen and $R_3$ is CHO. In the compound leucomycin $A_3$, R is hydroxy, $R_1$ is acetyl, $R_2$ is hydrogen and $R_3$ is CHO. Compounds of varying acyl groups ($R_1$) with R being a hydrogen or oxygen group have been isolated by direct fermentation in extremely low yields; ["Studies on the Macrolide Antibiotic YL-704 Complex," Akio Kinumaki, et al., *The Journal of Antibiotics*, Vol. XXVII, No. 2, pp. 117 – 122 (1974)]. The present invention provides a method for isolating these compounds with a greater efficiency than by direct fermentation. The present compounds are known to have a high antibiotic activity.

The present compounds are produced from niddamycin (1) the aldehyde group of which is first protected by conversion to niddamycin dimethyl acetal (2) by reaction with methanol in the presence of a carefully measured amount of a strong acid catalyst such as hydrochloric acid. The acid catalyst may also be a weak acid such as p-nitrobenzoic, chloroacetic or difluoroacetic acid added in sufficient amount to achieve a suitable reaction rate. The reaction can be carried out at temperatures of between 0° and 64°C. for times varying between a few hours to several weeks depending on the choice of acid catalyst, its concentration and the temperature of the reaction. This process minimizes acid catalyzed removal of the neutral sugar previously observed with strong acid solutions, as shown in [Omura, et al., *Chem. Pharm. Bull.* (Tokyo), 16, 1167 (1968)].

In a similar way the aldehyde groups of other known 16-membered macrolide antibiotics such as leucomycin $A_3$ or carbomycin B can also be protected by acid catalyzed dimethyl acetal formation.

In the preparation of carbomycin B, the intermediate niddamycin dimethyl acetal (2) is acylated with a mixture of acetic anhydride and pyridine to provide 2′, 3-di-(O)-acetylniddamycin dimethyl acetal (3B). This material, 2′, 3-di-(O)-acetyl-niddamycin dimethyl acetal (3B) on hydrolysis with sodium bicarbonate $NaHCO_3$) in an aqueous solution of methyl alcohol ($CH_3OH-H_2O$) yields 3-(O)-acetylniddamycin dimethyl acetal (6B). In this hydrolysis process, the 2′-acyl group, i.e. 2′-acetyl group, being vinical to the dimethylamino group is activated and hydrolyzed under mild basic conditions which do not hydrolye an unactivated acyl group such as that at the 3-position. The hydrolysis is carried out at 0° to 50°C. in the presence of a slight excess of bicarbonate in a mixture of an aqueous organic solvent. Although methanol is preferable as an organic solvent, other water-soluble solvents such as acetonitrile or ethanol may be used.

After hydrolysis of the 2′-(O)-acetyl group, the 3-(O)-acetylniddamycin dimethyl acetal (6B) is then reacted in a mixture of acetonitrile:water in the presence of an appropriate amount of difluoroacetic acid. This reaction hydrolyzes the dimethyl acetal group and results in the desired product, carbomycin B (7B).

In the synthesis of carbomycin B, where $R_1$ is acetyl, the intermediate dimethyl aceta (2) is acylated with a mixture of acetic anhydride and pyridine to provide 2′, 3-di-(O)-acetylniddamycin dimethyl acetal (3B). In the acylation of the intermediate niddamycin dimethyl acetal (2) other anhydrides may be used which would provide analogs of the 2′, 3-di-(O)-acetylniddamycin dimethyl acetal (3B). The other anhydrides that may be used include propionic anhydride (when $R_1 = R_2$ is propionyl), butyric anhydride (when $R_1 = R_2$ is butyryl) or a mixed anhydride such as formic acetic anhydride.

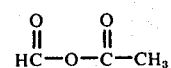

(when $R_1 = R_2$ is formyl). This material, 2′, 3-di-(O)-acylniddamycin dimethyl acetal (3), on hydrolysis with sodium bicarbonate ($NaHCO_3$) in an aqueus solution of methyl alcohol ($CH_3OH-H_2O$) yields 3-(O)-acylniddamycin dimethyl acetal (6). Thus, other products may be obtained depending upon the nature of the acylating agent as used to produce the dimethyl acetal (3). The product when $R_1$ is HCO, is 3-(O)-formylniddamycin dimethyl acetal (6A); when R₁ is propionyl (C₂H₅CO), the product is 3-(O)-propionylniddamycin dimethyl acetal (6C); and when R₁ is butyryl (C₃H₇CO), the product is 3-(O)-butyryl niddamycin dimethyl acetal (6D). In this hydrolysis process, the acyl group, e.g. propionyl (C₂H₅CO), being vicinal to the dimethylamino group is activated and hydrolyzed under mild basic conditions which do not hydrolyze an unactivated acyl group such as that at the 3-position.

Following hydrolysis of the 2′-(O)-acyl group, the dimethyl acetal group is removed by acid catalyzed hydrolysis using a determined amount of difluoroacetic acid in the mixed solvent of acetonitrile:water. These products are shown generally in the flow diagram below. However, they may be obtained where desired. The product when R₁ is HCO is 3-(O)-formylniddamycin (7A); when R₁ is C₂H₅CO, the product is 3-(O)-propionylniddamycin (7C); and when R₁ is C₃H₇CO the product is 3-(O)-butyrylniddamycin (7D).

The process of providing leucomycin A₁ (5), which is identical to 9-dihydroniddamycin B, is initiated with the reduction of the intermediate, niddamycin dimethyl acetal (2) which is reduced with sodium borohydride (NaBH₄) and methanol (CH₃OH) which provides a mixture of epimers in which leucomycin A₁ dimethyl acetal (9-dihydroniddamycin B dimethyl acetal) (4) predominates and is isolated by chromatography. The dimethyl acetal (4) yields the desired product, leucomycin A₁ (9-dihydroniddamycin B) (5), by hydrolysis with a solution of difluoroacetic acid in acetonitrile:water.

The reduction of 3-(O)-acetylniddamycin dimethyl acetal (6B) with sodium borohydride in methanol yields as the major reduced product, leucomycin A₃ dimethyl acetal, i.e. 3-(O)-acetyl-9-dihydroniddamycin B dimethyl acetal (8B) corresponding to the value of R₁ equal to CH₃CO as in the dimethyl acetal (6B). The product, accordingly, may be different such as when R₁ is HCO, the product is 3-(O)-formyl-9-dihydroniddamycin B dimethyl acetal (8A); when R₁ is propionyl (C₂H₅CO), the product is 3-(O)-propionyl-9-dihydroniddamycin B dimethyl acetal (8C); and when R₁ is butyryl (C₃H₇CO), the product is 3-(O)-butyryl-9-dihydroniddamycin B dimethyl acetal (8D). The reaction temperatures during the reduction range from 0° to 50°C. and the reduction is completed in 1 to 24 hours. Other solvents may be used such as ethyl alcohol or other alkali salts of the reducing agents such as lithium borohydride and sodium trimethyl borohydride [NaBH(OCH₃)₃].

The desired produce (9B), leucomycin A₃, i.e. (3-(O)-acetyl-9-dihydroniddamycin B), is provided by the hydrolysis of the dimethyl acetal (8B) in a mixed solvent of 50% acetonitrile:water (CH₃CN-H₂O) in the presence of about 2.5 equivalents of difluoroacetic acid as an acid catalyst. The organic solvent is not necessary for the reaction as the acid salt of the macrolide is sufficiently soluble in water. However, if he acetonitrile is not used, the amount of weak acid used must be less since the degree of ionization will increase thereby increasing the proton concentration in the reaction rate. Conversely if less water is used more of the acid catalyst must be used to maintain the same reaction rate. Depending on exact conditions, the reaction is complete in 2 to 20 hours at temperatures ranging from 0° to 50°C.

As with the product dimethyl acetal (8), the desired product (9), i.e. 3-(O)-acyl-9-dihydroniddamycin B, may be different and will vary as to the corresponding value of R₁. The various products that may be obtained with a different value of R₁ are 3-(O)-formyl-9-dihydroniddamycin B (9A) when R₁ is HCO; 3-(O)-propionyl-9-dihydroniddamycin B (9C) when R₁ is propionyl (C₂H₅CO); and 3-(O)-butyryl-9-dihydroniddamycin B (9D) when R₁ is butyryl (C₃H₇CO).

The synthesis of the compounds of this invention are provided in the flow charts below which have numerals to correspond with the structural compounds set forth above.

Flow Chart for Synthesis of Leucomycin A₁ (9-Dihydroniddamycin B)

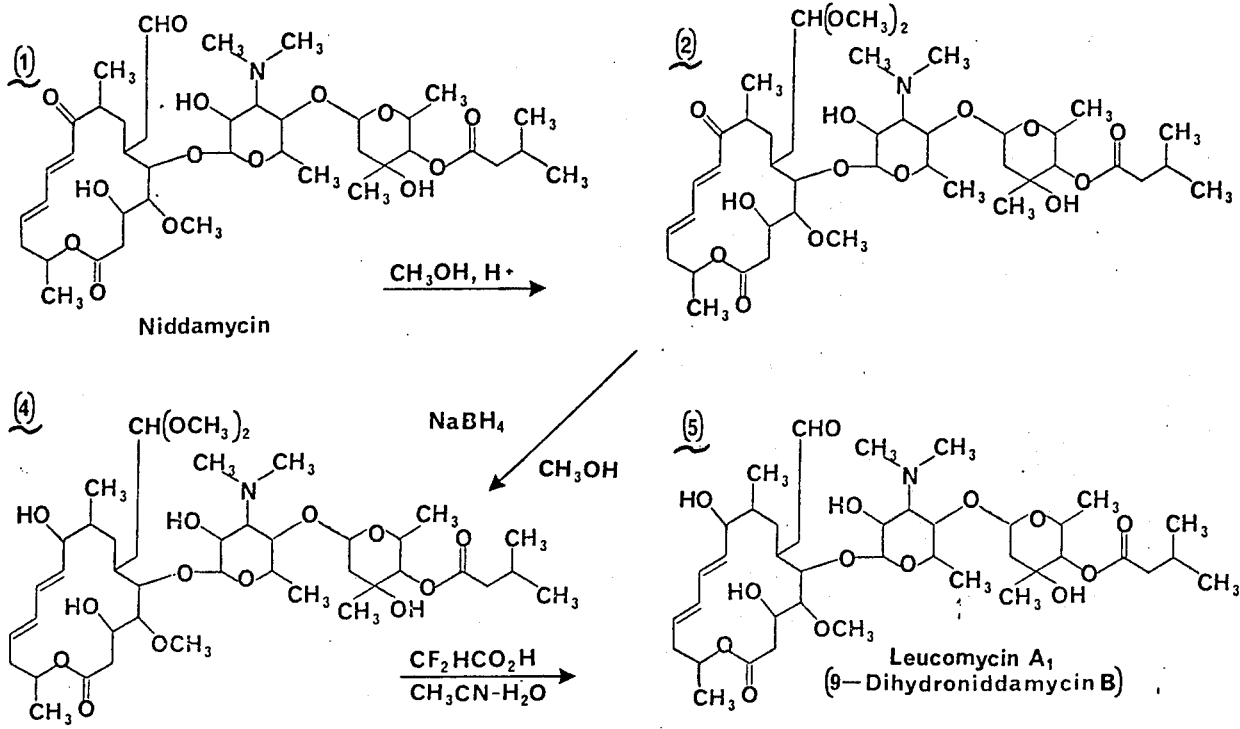

3,970,642

-continued
Flow Chart for Synthesis of Leucomycin A3 and Related 3-(Q)-Acyl-9-Dihydroniddamycin B Compounds

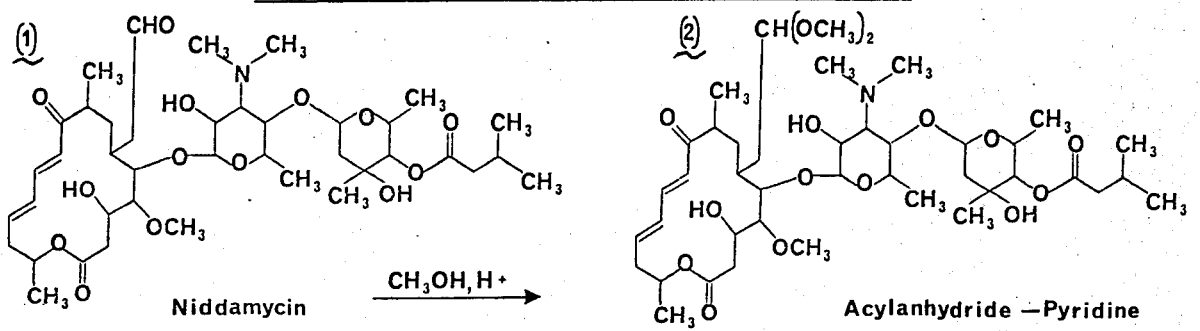

Niddamycin → CH₃OH, H⁺ → (2) → Acylanhydride —Pyridine →

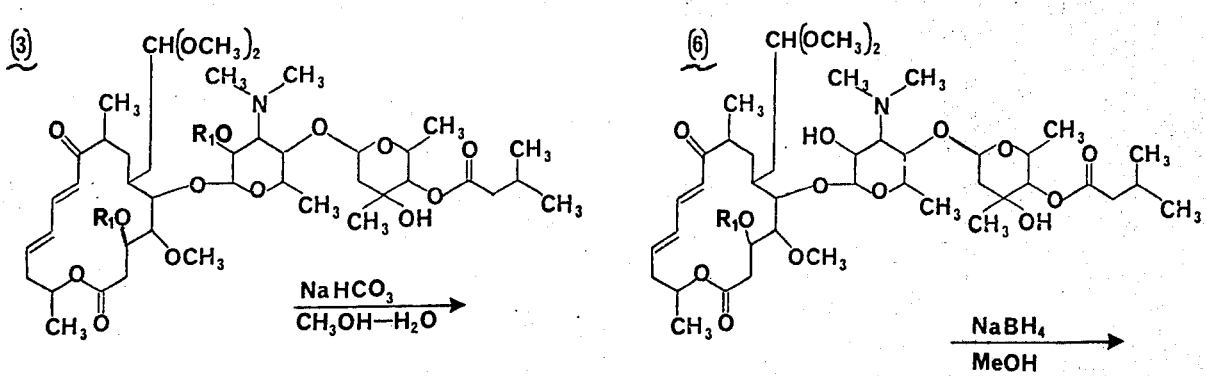

(3) → NaHCO₃ / CH₃OH—H₂O →   (6) → NaBH₄ / MeOH →

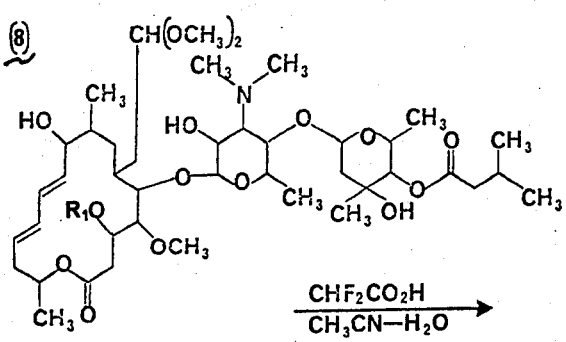

(3A) R₁ = HCO
(3B) R₁ = CH₃CO
(3C) R₁ = C₂H₅CO
(3D) R₁ = C₃H₇CO

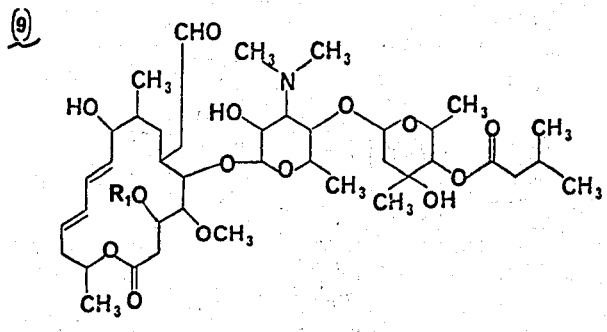

(6A) R₁ = HCO
(6B) R₁ = CH₃CO
(6C) R₁ = C₂H₅CO
(6D) R₁ = C₃H₇CO (8) → CHF₂CO₂H / CH₃CN—H₂O →   (9)

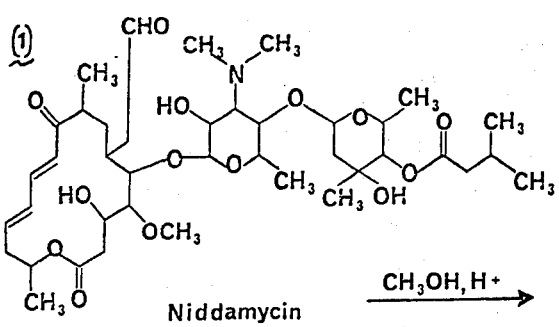

(8A) R₁ = HCO
(8B) R₁ = CH₃CO
(8C) R₁ = C₂H₅CO
(8D) R₁ = C₃H₇CO

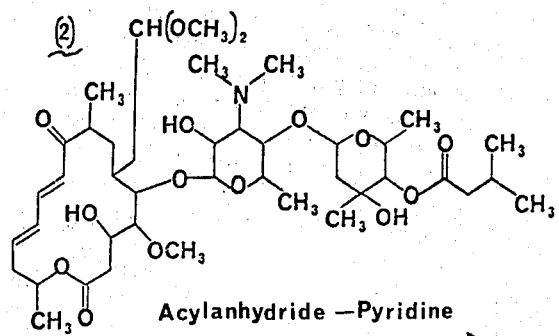

(9A) R₁ = HCO
(9B) R₁ = CH₃CO
(9C) R₁ = C₂H₅CO
(9D) R₁ = C₃H₇CO (1) Niddamycin → CH₃OH, H⁺ →   (2) → Acylanhydride —Pyridine →

Flow Chart for Synthesis of Carbomycin B and Related 3-(O)-Esters -continued

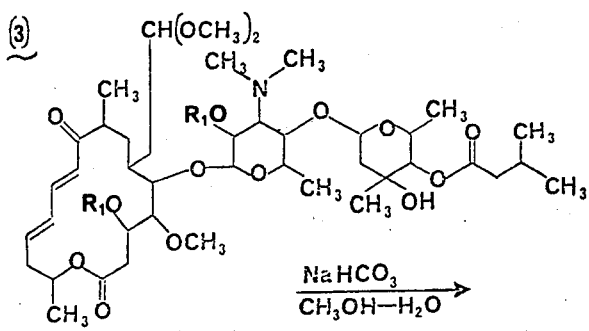

(3A) $R_1$ = HCO
(3B) $R_1$ = $CH_3CO$
(3C) $R_1$ = $C_2H_5CO$
(3D) $R_1$ = $C_3H_7CO$

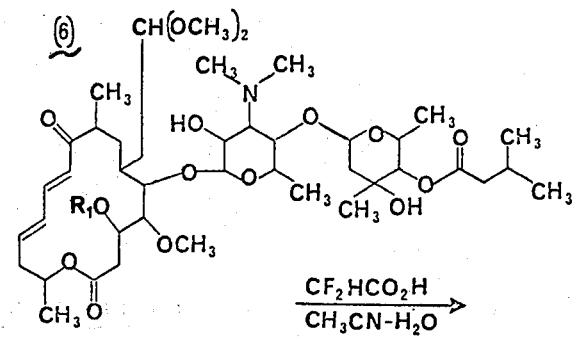

(6A) $R_1$ = HCO
(6B) $R_1$ = $CH_3CO$
(6C) $R_1$ = $C_2H_5CO$
(6D) $R_1$ = $C_3H_7CO$

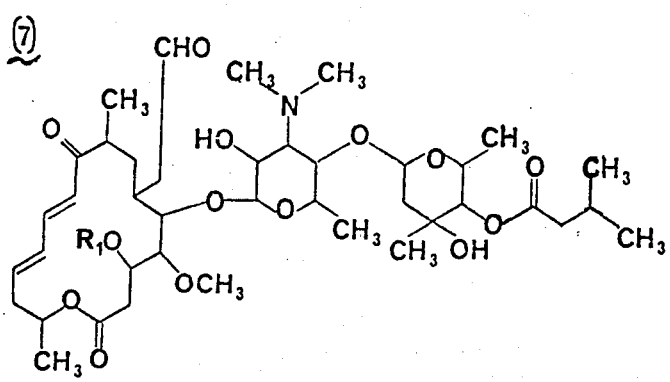

(7A) $R_1$ = HCO
(7B) $R_1$ = $CH_3CO$
(7C) $R_1$ = $C_2H_5CO$
(7D) $R_1$ = $C_3H_7CO$

The following examples further illustrate the compounds and means of preparing them according to the present invention. The number in parentheses following the chemical name identifies the compound by such specific number which may be alluded to in succeeding examples to identify the compounds by number and as corresponding and shown in the above flow chart of the synthesis of carbomycin B, leucomycin A₁ (9-dihydroniddamycin B) and related 3-(O)-esters such as leucomycin A₃ (3-(O)-acetyl-9-dihydroniddamycin B).

EXAMPLE I

Niddamycin Dimethyl Acetal (2)

The methanolic hydrochloric acid reagent employed for the preparation of (2) was prepared by mixing 22.4 ml. of concentrated HCl (37.3% HCl by weight, specific gravity at 15°/15°C. 1.189) with 3.79 liters of methanol.

A 50.00 g (0.06378 mole) sample of niddamycin was stirred while 875 ml. of the methanolic hydrochloric acid reagent was added. The reaction mixture was stirred while final adjustment of the pH was made by addition of acid reagent in 2.0 ml. portions. It was found that when the pH reached 3.0 as measured by Hydrion Test papers (range 3.0 – 5.0) dimethyl acetal formation proceeded at convenient rate without acid catalyzed degradation of the macrolide antibiotic. After standing for 24 hours at 25°C. the reaction was complete when checked by thin layer chromatography. A solution of 4.4 g. of $K_2CO_3$ in 20 ml. of water was added while stirring to quence further acid catalyzed reaction. The reaction mixture was then concentrated in vacuo to 200 ml. and was poured into 1.0 liter of water in which 4.4 g. of $K_2CO_3$ was dissolved. The product was extracted with 1 × 200 and 2 × 100 ml. portions of chloroform. The combined chloroform extracts were washed with 3 × 100 ml. portions of water – 1% $NaHCO_3$ – 2% $Et_3N$. The chloroform was dried over anhydrous $MgSO_4$ and was evaporated in vacuo. The residue was dissolved in 200 ml. of methanol and the methanol was evaporated in vacuo to remove residual chloroform. The residue was crystallized from methanol (170 ml.) — water (100 ml.) to give 35.3 g. of (2) after drying at 65° in a vacuum oven. The product was polymorphic undergoing a crystal change at 110° and melting at 203° – 208° in a sealed evacuated capillary; $[\alpha]_D^{25}$ −39.3° (C = 1.00, $C_2H_5OH$); $\lambda_{max}^{CH_3OH}$ 278 nm, = ε 22,750.

Analysis Calcd. for $C_{42}H_{71}NO_{15}$ (830.032): C: 60.78; H: 8.62; N: 1.69; O: 28.91. Found: C: 61.03; H: 8.70; N: 1.64; O: 29.06.

EXAMPLE II

Niddamycin Dimethyl Acetal — Procedure Employing Difluoroacetic Acid

A 15.00 g. (19.10 mmole) sample of niddamycin was dissolved in 225 ml. of methanol and 13.0 ml. (208 mmole) of difluoroacetic acid was added. The solution was stirred briefly and was allowed to stand at 25°C. for 66 hours. Then, the reaction mixture was poured into 1.0 liter of water containing 13.3 g. of $K_2CO_3$. The product was extracted with 1 × 500 and 1 × 250 ml. portions of benzene. The combined benzene extracts were washed with 3 × 150 ml. portions of 1% aqueous $NaHCO_3$ solution, were dried over $Na_2SO_4$, and were concentrated to 45 ml. To the concentrate was added 100 ml. of hexane and the product was allowed to crystallize overnight. The crystals were isolated and weighed 8.86 g. The product was recrystallized from methanol (40 ml.) — water (30 ml.) to give 7.03 g. of product which had m.p. 205° – 210°C.

EXAMPLE III

Niddamycin Dimethyl Acetal — Procedure Employing Chloroacetic Acid

A 15.00 g. (19.10 mmole) sample of niddamycin was dissolved in 225 ml. of methanol and 18.25 g. (193 mmole) of chloroacetic acid was added. The mixture was refluxed for 16.5 hours, was allowed to cool, and then was poured into 1.0 liter of water containing 13.3 g. of $K_2CO_3$. The product was extracted with 1 × 500 and 1 × 300 ml. portions of benzene. The combined benzene layers were washed with 3 × 150 ml. portions of 1% aqueous $NaHCO_3$ solution, were dried over $Na_2SO_4$, and were evaporated to give 15.7 g. of crude product after brief drying at 25°C. and 1.0 mm Hg. The sample was dissolved in 25 ml. of ethyl acetate with heating and 160 ml. of hexane was added. After crystallization was complete the product was isolated and dried to give 7.95 g. This sample was recrystallized from methanol (40 ml.) — water (35 ml.) to give 5.57 g. of product which had m.p. 106° – 112°C. (alternate polymorph).

EXAMPLE IV

Niddamycin Dimethyl Acetal — Procedure Employing p-Nitrobenzoic Acid

A 3.00 g. (3.83 mmole) sample of niddamycin was dissolved in 46 ml. of methanol and 6.45 g. (38.5 mmole) of p-nitrobenzoic acid was added. The acid was only partially soluble at 25°C. but dissolved completely at reflux. The mixture was refluxed for 70 hours and then was allowed to cool. The reaction mixture was diluted with 150 ml. of benzene and was washed first with 100 ml. of water containing 4.5 g. of KOH and then with 3 × 50 ml. portions of 1% aqueous $NaHCO_3$ solution. The benzene was dried over $NaSO_4$ and was evaporated to give 2.99 g. of crude product.

The crude sample was purified by chromatography on a column of 200 g. of silica gel employing benzene:1% N-methylmorpholine:0.36% methanol as the eluent system giving 1.66 g. of product. This material showed only one component by thin-layer chromatography.

EXAMPLE V

Carbomycin B Dimethyl Acetal — Procedure Employing Difluoroacetic Acid

A 400 mg. (0.484 mmole) sample of carbomycin B was dissolved in 6.0 ml. of methanol and 0.352 ml. (5.62 mmole) of difluoroacetic acid was added. After stirring briefly, the reaction mixture was allowed to stand at 25°C. for 624 hours. Then, the mixture was poured into 150 ml. of 1% aqueous $NaHCO_3$ solution, and the product was extracted with 1 × 50 and 3 × 25 ml. portions of benzene. The combined benzene extracts were washed with 2 × 25 ml. portions of 1% aqueous $NaHCO_3$ solution and were dried over $Na_2SO_4$. The benzene was evaporated leaving 384 mg. of crude product. The product was crystallized from methanol (3.2 ml.) — water (2.4 ml.) to yield 246 mg. of pure product which had m.p. 200° – 205°C.; $[\alpha]_D^{22}$ –14° (C = 1.00, EtOH); $\lambda_{max}^{MeOH}$ 278 nm, $\epsilon$=22,400; NMR ($CDCl_3$, 25°C.) three OMe groups at 3.07, 3.24 and 3.58 ppm., one $N(CH_3)_2$ group at 2.52 ppm. and one $OCOCH_3$ group at 2.04 ppm.

Analysis Calcd. for $C_{44}H_{73}NO_{16}$ (872.079): C: 60.60; H: 8.44; N: 1.61; O: 29.35. Found: C: 60.81; H: 8.77; N: 1.56; O: 29.57.

EXAMPLE VI

Leucomycin $A_3$ Dimethyl Acetal — Procedure Employing Difluoroacetic Acid

A 400 mg. (0.483 mmole) sample of leucomycin $A_3$ was dissolved in 6.0 ml. of methanol and 0.385 ml. (6.15 mmole) of difluoroacetic acid was added. After stirring briefly, the reaction mixture was allowed to stand at 25°C. for 840 hours. Then, the reaction mixture was poured into 150 ml. of 1% aqueous $NaHCO_3$ solution and the product was extracted with 1 × 50 and 3 × 25 ml. portions of benzene. The combined benzene extracts were washed with 3 × 25 ml. portions of 1% aqueous $NaHCO_3$ solution and were dried over $Na_2SO_4$. The benzene was evaporated leaving 385 mg. crude product. The product was purified by chromatography on a 35 g. column of silica gel using benzene:3% methanol as the eluent. The pure fractions were identified by thin-layer chromatography, were combined, and were evaporated to give 118 mg. of product after drying at 65°C. in a vacuum oven for 24 hours: amorphous; $[\alpha]_D^{22}$ –61.6° (C = 1.00, EtOH); $\lambda_{max}^{MeOH}$ 232 nm, $\epsilon$=28,200; NMR ($CDCl_3$, 25°C.) three OMe groups at 3.22, 3.28 and 3.54 ppm., one $N(CH_3)_2$ group at 2.52 ppm., one $OCOCH_3$ group at 2.11 ppm.

Analysis Calcd. for $C_{44}H_{75}NO_{16}$ (874.086): C: 60.46; H: 8.65; N: 1.60; O: 29.29. Found: C: 60.14; H: 8.75; N: 1.60; O: 29.18.

EXAMPLE VII

Leucomycin $A_1$ Dimethyl Acetal (9-Dihydroniddamycin B Dimethyl Acetal) (4)

A 3.00 g. (3.61 mmole) sample of niddamycin dimethyl acetal (2) was dissolved in 120 ml. of methanol and 0.452 g. (11.9 mmole) of sodium borohydride was added. The mixture was stirred at 25° for 40 minutes and was then poured into 1.0 liter of 1% aqueous $NaHCO_3$ solution. The product was extracted with 2 × 200 and 1 × 100 ml. portions of benzene. The combined benzene layers were washed with 2 × 100 ml. portions of 1% aqueous NaHCO$_3$ solution, were dried over Na$_2$SO$_4$, and were concentrated to give 2.886 g. of crude product after drying at 65° in a vacuum oven overnight. The product was purified by chromatography on 200 g. of silica gel by elution with benzene-3% methanol to give 1.709 g. of (4) as a glass; $[\alpha]_D^{25}$ −77.5° (C = 1.00, C$_2$H$_5$OH); $\lambda_{max}^{CH_3OH}$ 232 nm, $\epsilon$ = 28,500.

Analysis Calcd. for C$_{42}$H$_{73}$NO$_{15}$ (832.048): C: 60.63; H: 8.84; N: 1.68; O: 28.85. Found: C: 60.39; H: 8.96; N: 1.59; O: 28.79.

EXAMPLE VIII

Leucomycin A$_1$ (9-Dihydroniddamycin B) (5)

A 0.909 g. (1.092 mmole) sample of 9-dihydroniddamycin B dimethyl acetal (4) was dissolved in 3.42 ml. of acetonitrile and a solution of 0.199 g. (2.062 mmole) of difluoroacetic acid in 10.28 ml. of water was added. The mixture was allowed to stand at 25° for 24 hours and was then diluted with 100 ml. of 1% aqueous NaHCO$_3$ solution. The product was extracted with 2 × 75 ml. portions of benzene. The combined benzene extracts were dried over Na$_2$SO$_4$ and were evaporated in vacuo to give 0.727 g. of crude product. The sample was purified by chromatography on 100 g. of silica gel by elution with benzene — 4% methanol to give 0.394 g. of (4) as an amorphous solid; $[\alpha]_D^{22}$ −77.0° (C = 1.00, C$_2$H$_5$OH), −59.8° (C = 1.00, CHCl$_3$); $\lambda_{max}^{CH_3OH}$ 231 nm, $\epsilon$ = 27,000.

This sample had identical thin-layer chromatographic properties with an authentic sample of leucomycin A$_1$. Three elution systems were used with silica gel G plates: A; benzene-methanol-NH$_4$OH (85:15:1): B; methylene chloride-ethanol-NH$_4$OH (85:15:1): C; carbontetrachloride-dimethyl-formamide (20.5:2.5).

EXAMPLE IX

2′, 3-Di-(O)-Acetylniddamycin Dimethyl Acetal (3B)

A 5.43 g. (6.53 mmole) sample of (2) was dissolved in 25 ml. of pyridine and 2.7 ml. of acetic anhydride was added. The mixture was allowed to stand at 25° for 21 days. Then, 4 ml. of methanol was added and 3 hours later the mixture was diluted with 200 ml. of benzene. The benzene mixture was washed with 3 × 50 ml. portions of water—1% NaHCO$_3$, was dried over Na$_2$SO$_4$, and was evaporated in vacuo. The residue was redissolved in benzene and was re-evaporated to remove last traces of pyridine. The residue was dried at 55° in a vacuum oven overnight to give 5.88 g. of crude (3B). The sample was crystallized from ethyl acetate-hexane to give 3.88 g. of (3B); m.p. 178° − 181°; $[\alpha]_D^{25}$ −32.7° (C = 1.00, C$_2$H$_5$OH); $\lambda$max CH$_3$OH 278 nm, $\epsilon$ = 21,400.

Analysis Calcd. for C$_{46}$H$_{75}$NO$_{17}$ (914.108): C: 60.44; H: 8.27; N: 1.53; O: 29.76. Found: C: 60.26; H: 8.42; N: 1.49; O: 29.56.

EXAMPLE X 3-(O)-Acetylniddamycin Dimethyl Acetal (6B)

A 3.50 g. (3.83 mmole) sample of (3B) was suspended in 150 ml. of methanol and a solution of 0.756 g. of NaHCO$_3$ in 50 ml. of water was added. The reaction mixture was stirred at 25° for 7 days (the suspension of (3B) dissolved after 4 days). The mixture was concentrated at 25° − 30° under vacuum to 90 ml. and was diluted with 300 ml. of 1% aqueous NaHCO$_3$. The product was extracted with 2 × 100 and 4 × 50 ml. portions of benzene. The combined benzene extracts were washed with 2 × 50 ml. portions of 1% aqueous NaHCO$_3$, were dried over Na$_2$SO$_4$, and were evaporated to give 3.20 g. of crude (6B) after drying in a vacuum oven at 65° overnight. The product was purified by crystallization from methanol-water to give 2.42 g. of (6B) with m.p. 202° − 208°; $[\alpha]_D^{25}$ −10.5° (C = 1.00, C$_2$H$_5$OH); $\lambda$max CH$_3$OH 278 nm, $\epsilon$ = 21,800.

Analysis Calcd. for C$_{44}$H$_{73}$NO$_{16}$ (872.079): C: 60.60; H: 8.44; N: 1.61; O: 29.35. Found: C: 60.81; H: 8.77; N: 1.56; O: 29.57.

EXAMPLE XI

Leucomycin A$_3$ Dimethyl Acetal (3-(O)-Acetyl-9-Dihydroniddamycin B Dimethyl Acetal) (8B)

A 1.002 g. (1.14 mmole) sample of 3-(O)-acetylniddamycin dimethyl acetal (6B) was dissolved in 40 ml. of methanol and 0.121 g. (3.20 mmole) of sodium borohydride was added. The mixture was stirred at 25° for 30 minutes and was then poured into 250 ml. of 1% aqueous NaHCO$_3$ solution. The product was extracted with 3 × 75 and 1 × 50 ml. portions of benzene. The combined benzene extracts were washed with 2 × 50 ml. portions of 1% aqueous NaHCO$_3$ solution, were dried over Na$_2$SO$_4$ and were evaporated to give 0.991 g. of crude product after drying in a vacuum oven overnight. The crude product was purified by chromatography on 100 g. of silica gel by elution with benzene — 3% methanol to give 0.569 g. of (8B) as an amorphous solid; $[\alpha]_D^{25}$ −64.0° (C = 1.00, C$_2$H$_5$OH); $\lambda$max CH$_3$OH 232 nm, $\epsilon$ = 28,250.

Analysis Calcd. for C$_{44}$H$_{75}$NO$_{16}$ (874.086): C: 60.46; H: 8.65; N: 1.60; O: 29.29. Found: C: 60.14; H: 8.75; N: 1.60; O: 29.18.

EXAMPLE XII

Leucomycin A$_3$ (3-(O)-Acetyl-9-Dihydroniddamycin B) (9B)

A 0.316 g. (0.362 mmole) sample of 3-(O)-acetyl-9-dihydroniddamycin B dimethyl acetal (8B) was dissolved in 2.42 ml. of acetonitrile and a solution of 0.093 g. (0.98 mmole) of difluoroacetic acid in 2.42 ml. of water was added. The mixture was allowed to stand at 25° for 24 hours and was then diluted with 60 ml. of 1% aqueous NaHCO$_3$ solution and 100 ml. of benzene. After thorough mixing, the layers were separated and the aqueous layer was extracted with 25 ml. of benzene. The combined benzene layers were washed with 2 × 15 ml. portions of 1% aqueous NaHCO$_3$ solution, were dried over Na$_2$SO$_4$ and were evaporated to give 0.292 g. of crude product. This product was purified by chromatography on 50 g. of silica gel by elution with benzene — 3% methanol to give 0.164 g. of (9B). The sample was crystallized from benzene, m.p. 127 − 129° C.; $[\alpha]_D^{24}$ −69.1° (C = 1.00, C$_2$H$_5$OH); $\lambda$max CH$_3$OH 231 nm, $\epsilon$ = 28,100.

This sample had thin-layer chromatographic properties identical to an authentic sample of leucomycin A$_3$ in solvent systems A, B and C.

EXAMPLE XIII

Carbomycin B (7B)

A 0.500 g. (0.573 mmole) sample of (6B) 3-(O)-acetylniddamycin dimethyl acetal) was suspended in 2.0 ml. of acetonitrile and a solution of 0.083 g. (0.860 mmole) of difluoroacetic acid in 6.0 ml. of water was added. After brief stirring, (6B) dissolved and the mixture was allowed to stand at 25°C. for 96 hours. The reaction mixture was then diluted with 100 ml. of 1% aqueous NaHCO$_3$ solution and the product was extracted with 2 × 40 ml. portions of benzene. The combined benzene extracts were washed with 2 × 40 ml. portions of 1% aqueous NaHCO$_3$ solution, were dried over Na$_2$SO$_4$ and were evaporated in vacuo to give after drying at 65° in a vacuum oven 0.383 g. of crude product. The product was purified by chromatography on 50 g. of silica gel by elution with benzene - 3% methanol to give 0.230 g. of (7B). The sample was crystallized from acetone - water, m.p. 193 - 200°C.; $[\alpha]_D^{25}$ −37.3° (C = 1.00, CHCl$_3$); λmax CH$_3$OH 278 nm, ε= 23,200.

Analysis Calcd. for C$_{42}$H$_{67}$NO$_{15}$ (826.000): C: 61.07; H: 8.18; N: 1.69. Found: C: 61.28; H: 8.48; N: 1.65.

The following examples and tables further illustrate the usefulness of the present compounds as active antimicrobials.

EXAMPLE XIV

Three niddamycin and two dihydroniddamycin compounds were tested for their activity against *Streptococcus pyogenes* C203, and *Diplococcus pneumoniae* 6301 and *Mycoplasma pneumoniae* FH.

A standard two-fold tube dilution test was used. The medium inoculum were varied with each culture.

In the test for activity against *Streptococcus pyogenes* C203, 5 ml. portions of brain-heart infusion broth were used with 0.1 ml. of 1:100 dilution culture. The test was incubated for 24 hours at 37°C.

In the test for activity against *Diplococcus pneumoniae* 6301, 5 ml. portions of brain-heart infusion broth and 20% horse serum were used with 0.1 ml. of 1:100 dilution culture. The test was incubated for 24 hours at 37°C.

In the test for activity against *Mycoplasma pneumoniae* FH, 4.5 ml. portions of PPLO broth were used with 0.5 ml. of 1:100 dilution culture. The test was incubated for six days at 37°C. The compounds tested are:

| | | |
|---|---|---|
| 2 | — | Niddamycin dimethyl acetal |
| 3B | — | 2′,3-Di-(O)-acetylniddamycin dimethyl acetal |
| 6B | — | 3-(O)-Acetylniddamycin dimethyl acetal |
| 4 | — | 9-Dihydroniddamycin B dimethyl acetal |
| 8B | — | 3-(O)-Acetyl-9-dihydroniddamycin B dimethyl acetal |

The results of the tests for the activity of the compounds are provided below in Table 1.

Table 1

| | Minimum Inhibitory Concentration meg./ml. | | |
|---|---|---|---|
| Compound | Streptococcus pyogenes C203 | Diplococcus pneumoniae 6301 | Mycoplasma pneumoniae FH |
| 2 | 0.78 | ≤ 1.56 | 25 |
| 3B | >100 | >100 | >100 |
| 6B | 12.5 | >12.5 | —≤50 | 25 |
| 4 | 6.2 | > 1.56 | —≤12.5 | 50 |
| 8B | 25 | >12.5 | —≤100 | 50 |

I claim:
1. A compound having the structural formula

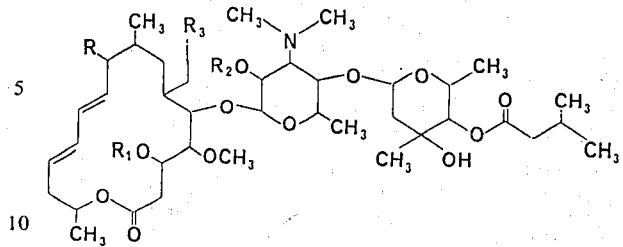

wherein R is oxygen, R$_1$ is hydrogen, HCO, CH$_3$CO, CH$_3$CH$_2$CO or CH$_3$CH$_2$CH$_2$CO; where R$_2$ is hydrogen or equivalent to R$_1$ and R$_3$ is CH(OCH$_3$)$_2$.

2. A compound according to claim 1, wherein R is oxygen, R$_1$ and R$_2$ are HCO, and R$_3$ is CH(OCH$_3$)$_2$.

3. A compound according to claim 2 named 2′, 3-di-(O)-formylniddamycin dimethyl acetal.

4. A compound according to claim 1 wherein R is oxygen, R$_1$ and R$_2$ are CH$_3$CO, and R$_3$ is CH(OCH$_3$)$_2$.

5. A compound according to claim 4 named 2′, 3-di-(O)-acetylniddamycin dimethyl acetal.

6. A compound according to claim 1 wherein R is oxygen, R$_1$ and R$_2$ are C$_2$H$_5$CO, and R$_3$ is CH(OCH$_3$)$_2$.

7. A compound according to claim 6 named 2′, 3-di-(O)-propionylniddamycin dimethyl acetal.

8. A compound according to claim 1 wherein R is oxygen, R$_1$ and R$_2$ are C$_3$H$_7$CO, and R$_3$ is CH(OCH$_3$)$_2$.

9. A compound according to claim 8 named 2′, 3-di-(O)-butyrylniddamycin dimethyl acetal.

10. A compound according to claim 1 wherein R is oxygen, R$_1$ is HCO, R$_2$ is H and R$_3$ is CH(OCH$_3$)$_2$.

11. A compound according to claim 10 named 3-(O)-formylinddamycin dimethyl acetal.

12. A compound according to claim 1 wherein R is oxygen, R$_1$ is CH$_3$CO, R$_2$ is H and R$_3$ is CH(OCH$_3$)$_2$.

13. A compound according to claim 12 named 3-(O)-acetylniddamycin dimethyl acetal.

14. A compound according to claim 1 wherein R is oxygen, R$_1$ is C$_2$H$_5$CO, R$_2$ is H, and R$_3$ is CH(OCH$_3$)$_2$.

15. A compound according to claim 14 named 3-(O)-propionylniddamycin dimethyl acetal.

16. A compound according to claim 1 wherein R is oxygen, R$_1$ is C$_3$H$_7$CO, R$_2$ is H, and R$_3$ is CH(OCH$_3$)$_2$.

17. A compound according to claim 16 named 3-(O)-butyrylniddamycin dimethyl acetal.

18. A compound according to claim 1 wherein R is hydroxy, R$_1$ is HCO, R$_2$ is H and R$_3$ is CH(OCH$_3$)$_2$.

19. A compound according to claim 18 named 3-(O)-formyl-9-dihydroniddamycin B dimethyl acetal.

20. A compound according to claim 1 wherein R is hydroxy R$_1$ is C$_2$H$_5$CO, R$_2$ is H, and R$_3$ is CH(OCH$_3$)$_2$.

21. A compound according to claim 20 named 3-(O)-propionyl-9-dihydroniddamycin B dimethyl acetal.

22. A compound according to claim 1 wherein R is hydroxy, R$_1$ is C$_3$H$_7$CO, R$_2$ is H, and R$_3$ is CH(OCH$_3$)$_2$.

23. A compound according to claim 22 named 3-(O)-butyryl-9-dihydroniddamycin B dimethyl acetal.

24. A compound according to claim 1 wherein R is oxygen, R$_1$ is H, R$_2$ is H and R$_3$ is CH(OCH$_3$)$_2$.

25. A compound according to claim 24 named niddamycin dimethyl acetal.

* * * * *